US00PP17883P2

(12) United States Plant Patent
Pierce

(10) Patent No.: US PP17,883 P2
(45) Date of Patent: Jul. 24, 2007

(54) ***CALIBRACHOA* PLANT NAMED 'CAL DEPYEL'**

(50) Latin Name: ***Calibrachoa* sp.**
Varietal Denomination: Cal Depyel

(75) Inventor: Robert Osteen Pierce, Watsonville, CA (US)

(73) Assignee: Goldsmith Seeds, Inc., Gilroy, CA (US)

( * ) Notice: Subject to any disclaimer, the term of this patent is extended or adjusted under 35 U.S.C. 154(b) by 0 days.

(21) Appl. No.: 11/352,963

(22) Filed: Feb. 13, 2006

(51) Int. Cl.
*A01H 5/00* (2006.01)

(52) U.S. Cl. ..... Plt./263
(58) Field of Classification Search ..... Plt./263
See application file for complete search history.

*Primary Examiner*—Anne Marie Grunberg
*Assistant Examiner*—S. B. McCormick-Ewoldt
(74) *Attorney, Agent, or Firm*—Jondle & Associates P.C.

(57) ABSTRACT

A new *Calibrachoa* plant particularly distinguished by medium-sized, deep-yellow flowers, an early to moderately-early and continuous flowering response, grass-green to deep-green, glossy foliage with lanceolate leaves, moderately vigorous growth, a medium-sized and spreading to prostrate plant habit, with strong branches, is disclosed.

2 Drawing Sheets

Genus and species: *Calibrachoa* sp.
Variety denomination: 'Cal Depyel'.

BACKGROUND OF THE NEW PLANT

The present invention comprises a new and distinct cultivar of *Calibrachoa,* botanically known as *Calibrachoa* sp., and hereinafter referred to by the cultivar name 'Cal Depyel'. The new cultivar originated from a hybridization made in July 2002 in Gilroy, Calif. The female parent was the proprietary deep-yellow flowered *Calibrachoa* plant '471-1' (unpatented), while the male parent was the proprietary *Calibrachoa* plant '465-1' (unpatented) having deep yellow flowers. The seeds produced by the hybridization were sown in January 2003 in Gilroy, Calif. A single plant selection was chosen for further evaluation and for asexual propagation in Summer 2004 in Gilroy, Calif.

The new cultivar was created in 2002 in Gilroy, Calif. and has been asexually reproduced repeatedly by vegetative cuttings and tissue culture in Gilroy, Calif. over a two-year period. 'Cal Depyel' has not been observed under all possible environmental conditions. The present invention has been found to retain its distinctive characteristics through successive asexual propagations.

Plant Breeder's Rights for this cultivar were applied for in Canada on Mar. 31, 2005, in Switzerland on Sep. 16, 2005 and with the European Union on Sep. 28, 2005.

SUMMARY OF THE INVENTION

The following are the most outstanding and distinguishing characteristics of this new cultivar when grown under normal horticultural practices in Gilroy, Calif. and Hillscheid, Germany.

1. Medium-sized, deep-yellow flowers;
2. Green-green to deep-green, glossy foliage with lanceolate leaves;
3. Moderately vigorous growth with strong branches;
4. A medium-sized and spreading to prostate or trailing plant habit; and 5. An early to moderately early and a continuous flowering response.

DESCRIPTION OF PHOTOGRAPHS

This new *Calibrachoa* plant is illustrated by the accompanying photographs which show overall plant habit including blooms, buds, and foliage of the plant; the colors shown are as true as can be reasonably obtained by conventional photographic procedures. The photographs are of a whole plant about 11-weeks old, grown in a greenhouse in Hillscheid, Germany, in May of 2005.

DESCRIPTION OF THE NEW CULTIVAR

Figure 1:
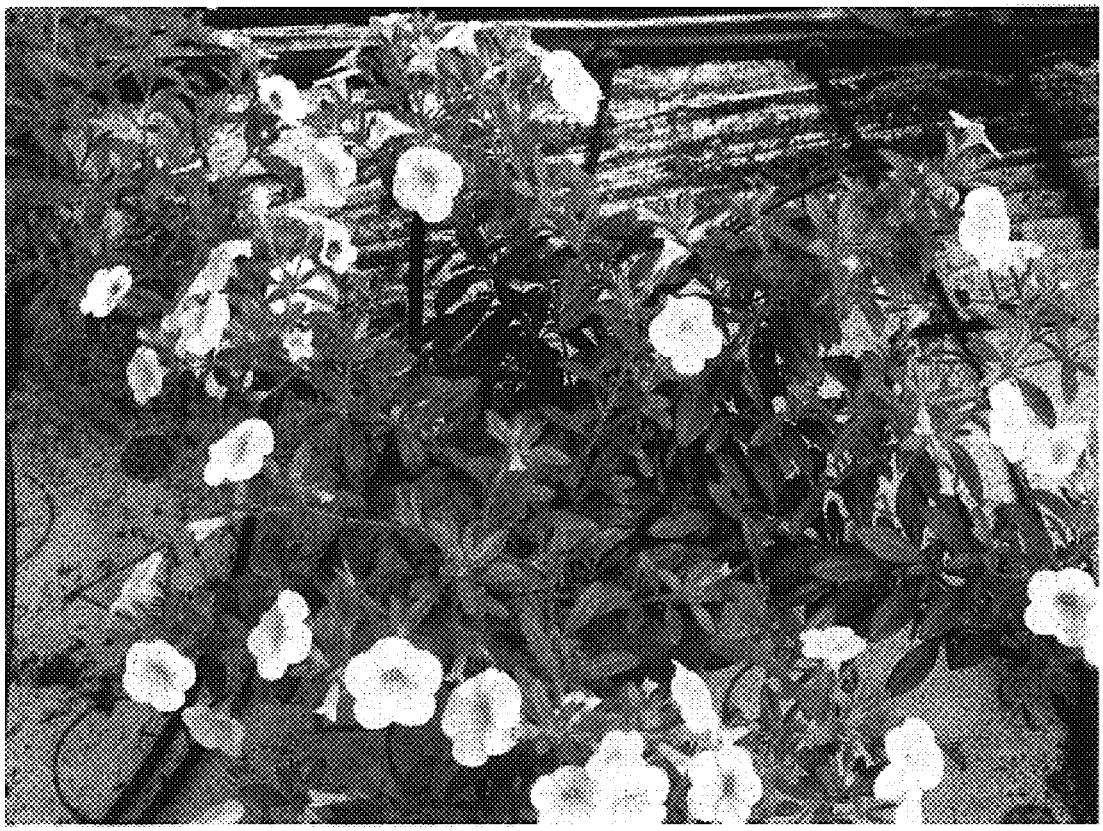
FIG. 1 shows the overall plant habit, including blooms, buds and foliage.
Figure 2:
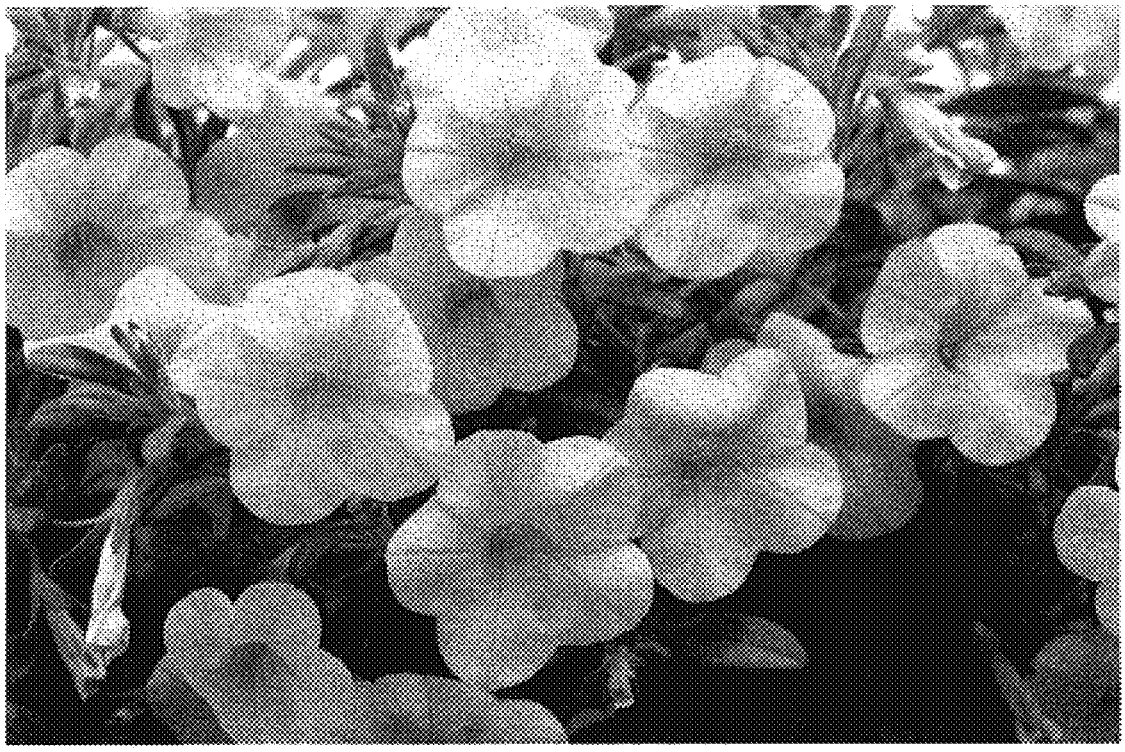
FIG. 2 shows a close-up of the mature inflorescences.

The following detailed description sets forth the distinctive characteristics of 'Cal Depyel'. The data which define these characteristics were collected from asexual reproductions carried out in Hillscheid, Germany. The plant history was taken on 6-week old unpinched plants which were planted as rooted cuttings in 12-cm pots in July 2005, and then grown in a greenhouse. Observations were made when the plants were in full flower in August 2005. Color readings were taken under natural light in the greenhouse. Color references are primarily to The R.H.S. Colour Chart of The Royal Horticultural Society of London (R.H.S.) (2001).

DETAILED BOTANICAL DESCRIPTION OF THE NEW PLANT

Classification:
*Family.*—Solanaceae.
*Botanical.*—*Calibrachoa* sp.
*Common name.*—*Calibrachoa.*

Parentage:
*Female parent.*—'471-1' a proprietary deep-yellow flowered *Calibrachoa* plant (unpatented).
*Male parent.*—'465-1', a proprietary deep-yellow flowered *Calibrachoa* plant (unpatented).

Growth:

*Form.*—Herbaceous perennial, usually cultivated as an annual plant.

*Habit.*—Spreading initially, later overhanging or trailing with fair branching; should be pinched once to enhance basal branching.

*Height* (*measured from the top of the soil*).—12.3 cm.

*Width* (*horizontal plant diameter*).—42.3 cm.

*Propagation.*—Terminal tips for cuttings.

*Time to produce a finished flowering plant.*—10 to 11 weeks for a 12-cm pot.

*Outdoor plant performance.*—For hanging baskets and container planting.

*Time to initiate and develop roots.*—About 21 days.

*Root description.*—Fibrous, self-branching

Stems:

*Average number* (*basal plus secondary*).—11.4.

*Length of basal branches* (*from center of the plant to the tips*).—24.6 cm.

*Internode length.*—1.3 cm to 2.5 cm.

*Diameter of branches* (*from midpoint*).—0.3 cm.

*Stem color.*—RHS 143C (green).

*Texture.*—Covered with dense pubescence.

*Anthocyanin.*—Absent.

Leaves:

*Arrangement.*—Initially alternate and later appearing opposite at flowering branches.

*Size.*—Length: 4.7 cm. Width: 1.5 cm.

*Shape.*—Elliptic (narrow).

*Margin.*—Entire.

*Apex.*—Acute to obtuse.

*Base.*—Attenuate.

*Color* (*mature leaves*).—Upper surface: Deeper than RHS 143A (deep grass-green), between RHS 141A and RHS 143A. Lower surface: RHS 137D.

*Texture.*—Appears glossy and nearly glabrous.

*Venation.*—Pinnate but indistinct, apart from the midrib.

*Venation color.*—RHS 145B for the lower surface.

*Variegation.*—None.

*Petioles.*—Length: 0.1 cm to 0.3 cm. Width: 0.1 cm to 0.2 cm. Color: RHS 144A. Texture: Covered with dense pubescence.

Flower bud:

*Shape.*—Tube-shaped or narrow funnel-shaped, with the lobes folded lengthwise.

*Size.*—Length: 2.0 cm when beginning to unfold. Diameter: Funnel is 0.4 cm; 0.5 cm to 0.7 at the tip.

*Color at tight bud.*—RHS 1B (greenish-yellow).

Inflorescence:

*Blooming habit.*—Continuous from Spring to Fall, nearly year-round.

*Inflorescence type.*—Flowers appear solitary, emerging from the leaf axils.

*Floret type.*—Base is funnel shaped; upper lobes open outward, salver-shaped and slightly zygomorphic.

*Number of flowers per node.*—One.

*Lastingness of individual blooms on the plant.*—6 days.

*Size.*—Diameter (flower face): 2.8 cm to 3.1 cm. Length (flower face): 2.8 cm to 3.1 cm. Depth (total length of flower): 2.1 cm.

*Funnel.*—Length (from below): 1.7 cm. Diameter (at opening): 0.7 cm to 0.9 cm.

*Fragrance.*—Weak, petunia-like.

*Peduncles.*—Color: RHS 144A. Length: 2.5 cm. Diameter: 0.1 cm. Texture: Pubescent.

Flowers:

*Immature flower.*—Diameter: 2.5 cm to 2.8 cm. Color: RHS 9A (deep yellow).

*Mature flower color.*—Upper surface: RHS 9A to RHS 9B, uniform. Lower surface: RHS 9C, with very fine lines or mid-veins of RHS 151B (green-yellow).

*Corolla.*—Shape of corolla: Tube-shaped. Color inside: Slightly more greenish than RHS 9B. Color outside: RHS N144B (yellow-green). Outside texture: Covered with dense glandular hair.

*Petals.*—Shape: Lower part fused, upper part is a free lobe. Apex: Rounded, retuse. Base: Fused. Margin: Entire. Waviness of petals: None or very little. Lobation: Weak. Texture: Smooth.

*Sepals.*—Shape: Lanceolate. Apex: Acute. Base: Fused. Margin: Entire. Length: 1.1 cm. Width: 0.2 cm. Color: RHS 137D (green) to RHS 137A at tips. Texture: Pubescent (covered with dense hair). Pubescence color: Whitish.

Reproductive organs:

*Stamens.*—Number: 5 (various lengths). Filament color: RHS 155A (whitish). Filament length: 0.5 cm to 1.0 cm. Filament diameter: 0.1 cm. Pollen color: RHS 10B (yellow). Pollen quantity: Moderate.

*Pistils.*—Number: 1. Length: 1.0 cm. Diameter: 0.1 cm. Stigma color: RHS 145B (light-green). Style color: RHS 145C (pale-green).

Fruit and seed set: No seed set observed.

Disease and insect resistance: No particular resistance or susceptibility has been observed.

COMPARISON WITH PARENTAL AND COMMERCIAL CULTIVARS

'Cal Depyel' differs from the female parent '471-1' (unpatented) by having smaller leaves, a more prostrate plant habit and an earlier flowering response than '471-1'.

'Cal Depyel' differs from the male parent '465-1' (unpatented) by having larger flowers than '465-1'. In addition, 'Cal Depyel' develops more basal branches, and at a later stage, develops more flowers in the center of the plant than '465-1'.

'Cal Depyel' differs from the commercial cultivar 'Cal Yel' (U.S. Plant Pat. No. 14,464) by having larger, deep and more uniform yellow flowers than 'Cal Yel' (RHS 9A for 'Cal Depyel' compared to RHS 10A for 'Cal Yel'). In addition, 'Cal Depyel' has brighter green foliage and fewer but stronger branches with longer internodes than 'Cal Yel'.

I claim:

1. A new and distinct cultivar of *Calibrachoa* plant as shown and described herein.

* * * * *